US008546072B2

(12) United States Patent
Kitagawa et al.

(10) Patent No.: US 8,546,072 B2
(45) Date of Patent: Oct. 1, 2013

(54) SUBSTRATE FOR ASSAYING β-GLUCAN AND/OR ENDOTOXIN AND ASSAY METHOD

(75) Inventors: Takeshi Kitagawa, Amagasaki (JP); Naoyuki Yamamoto, Amagasaki (JP); Mutsuhiro Date, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 375 days.

(21) Appl. No.: 12/918,724

(22) PCT Filed: Feb. 20, 2009

(86) PCT No.: PCT/JP2009/053042
§ 371 (c)(1),
(2), (4) Date: Aug. 20, 2010

(87) PCT Pub. No.: WO2009/104741
PCT Pub. Date: Aug. 27, 2009

(65) Prior Publication Data
US 2010/0330700 A1    Dec. 30, 2010

(30) Foreign Application Priority Data
Feb. 22, 2008   (JP) ................................ 2008-040967

(51) Int. Cl.
*A61K 38/00* (2006.01)
*A61K 38/04* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)
*C12Q 1/00* (2006.01)
*G01N 33/53* (2006.01)

(52) U.S. Cl.
USPC ................. 435/4; 435/7.1; 530/300; 530/330

(58) Field of Classification Search
None
See application file for complete search history.

(56) References Cited

U.S. PATENT DOCUMENTS

| 4,576,745 | A | | 3/1986 | Monsigny |
| 5,994,501 | A | * | 11/1999 | Ruoslahti et al. ............. 530/324 |
| 6,194,190 | B1 | * | 2/2001 | Izu et al. ...................... 435/227 |
| 2005/0214890 | A1 | * | 9/2005 | Tan et al. ........................ 435/23 |

FOREIGN PATENT DOCUMENTS

| JP | 57-502266 A | | 12/1982 |
| JP | 59-019532 B | | 5/1984 |
| JP | 61-54400 B2 | | 11/1986 |
| JP | 08-034796 A | | 2/1996 |
| WO | WO 9840738 A1 | * | 9/1998 |
| WO | WO 00/61789 A1 | | 10/2000 |
| WO | WO 02061038 A2 | * | 8/2002 |
| WO | WO 2009020877 A2 | * | 2/2009 |

OTHER PUBLICATIONS

Morita et al. Journal of Biochemistry 1977 82:1495-1498.*
Bugaj et al. Journal of Biomedical Optics 2001 6:122-133.*
Hermanson Bioconjugate Techniques San Diego: Elsevier 1996 297-302 and 354-357.*
Kang et al. Journal of Nanobiotechnology 2011 9:1-13.*
Zimmerman et al. Proceedings of the National Academy of Sciences 1978 75:750-753.*
Technical bulletin for the factor Xa removal kit from Sigma (1999).*
Bond et al., *Analytical Biochemistry*, 155: 315-321 (1986).
Srimal et al., *Journal of Biochemistry*, 98: 305-318 (1985).
Stocker et al., *Biochemistry*, 29: 10418-10425 (1990).

* cited by examiner

*Primary Examiner* — Robert A Wax
*Assistant Examiner* — Caralynne Helm
(74) *Attorney, Agent, or Firm* — Leydig, Voit & Mayer, Ltd.

(57) ABSTRACT

An object of the present invention is to provide a peptide derivative for determining β-glucan or endotoxin which allows high sensitivity measurement, and a method for determining β-glucan and/or endotoxin using the same. The present invention relates to (1) a peptide derivative represented by the following general formula [1]:

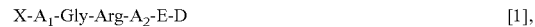

$X\text{-}A_1\text{-}Gly\text{-}Arg\text{-}A_2\text{-}E\text{-}D$  [1], (2) a reagent for determining β-glucan and/or endotoxin comprising the above-described peptide derivative, (3) a method for determining β-glucan and/or endotoxin, characterized in that a sample containing β-glucan and/or endotoxin, an amebocyte lysate of a horseshoe crab and the above-described peptide derivative are reacted each other, then the resulting released compound represented by the following general formula [2]:

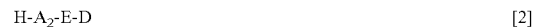

$H\text{-}A_2\text{-}E\text{-}D$  [2]

is separated from unreacted substance and quantified, and the determination is made based on this value, and (4) a reagent kit for determining β-glucan and/or endotoxin, comprising an amebocyte lysate of a horseshoe crab and the above-described peptide derivative as constituents thereof.

10 Claims, 4 Drawing Sheets

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: substrate

<400> SEQUENCE: 1

Thr Gly Arg Gly
1

<210> SEQ ID NO 2
<211> LENGTH: 4
<212> TYPE: PRT
<213> ORGANISM: Artificial Sequence
<220> FEATURE:
<223> OTHER INFORMATION: substrate

<400> SEQUENCE: 2

Thr Gly Arg Lys
1

<210> SEQ ID NO 3
<211> LENGTH: 4
<212> TYPE: PRT
<213> ORGANISM: Artificial Sequence
<220> FEATURE:
<223> OTHER INFORMATION: substrate

<400> SEQUENCE: 3

Thr Gly Arg Thr
1

<210> SEQ ID NO 4
<211> LENGTH: 4
<212> TYPE: PRT
<213> ORGANISM: Artificial Sequence
<220> FEATURE:
<223> OTHER INFORMATION: substrate

<400> SEQUENCE: 4

Thr Gly Arg Asn
1

<210> SEQ ID NO 5
<211> LENGTH: 4
<212> TYPE: PRT
<213> ORGANISM: Artificial Sequence
<220> FEATURE:
<223> OTHER INFORMATION: substrate

<400> SEQUENCE: 5

Thr Gly Arg Thr
1

<210> SEQ ID NO 6
<211> LENGTH: 4
<212> TYPE: PRT
<213> ORGANISM: Artificial Sequence
<220> FEATURE:
<223> OTHER INFORMATION: substrate

<400> SEQUENCE: 6

Ser Gly Arg Gly

```
<210> SEQ ID NO 7
<211> LENGTH: 4
<212> TYPE: PRT
<213> ORGANISM: Artificial Sequence
<220> FEATURE:
<223> OTHER INFORMATION: substrate

<400> SEQUENCE: 7

Leu Gly Arg Gly
1
```

SUBSTRATE FOR ASSAYING β-GLUCAN AND/OR ENDOTOXIN AND ASSAY METHOD

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,296 bytes ASCII (Text) file named "706799SequenceListing.txt," created Aug. 12, 2010.

TECHNICAL FIELD

The present invention relates to a novel peptide derivative useful as a substrate for determining (assaying) activity of clotting enzyme which is activated by a reaction of (1→3)-β-D-glucan (hereinafter referred to as β-glucan) and/or endotoxin with an amebocyte lysate of a horseshoe crab, and a method for determining β-glucan and/or endotoxin using said derivative.

BACKGROUND ART

Endotoxin is lipopolysaccharide (LPS) present in outer membrane of cell wall of gram-negative bacteria, and has been known as a potent pyrogen. For this reason, detection of endotoxin is considered important in the injectable pharmaceuticals and the like, and the test method of endotoxin has been described in pharmacopeia of the United States, Japan and other countries. In addition, the endotoxin is considered to be a main cause of a shock in gram-negative bacterial infection, and in the clinical diagnosis, determination of plasma endotoxin level is used for the diagnosis of gram-negative bacterial infection, determination of therapeutic effect and prognosis of therapy for gram-negative bacterial infection, and earlier diagnosis for endotoxin shock and so on. On the other hand, β-glucan is known as one of the main cell wall constituents of many pathogenic fungi, and in the clinical diagnosis, determination of plasma or serum β-glucan level is employed for earlier diagnosis of the fungal infection, and determination of therapeutic effect and prognosis.

With respect to the method for determining endotoxin and/or β-glucan, a variety of methods through the utilization of effects of plural protease precursors (Factor C, Factor G, Factor B, proclotting enzyme, coagulogen) which are activated by the reaction of an amebocyte lysate of a horseshoe crab with endotoxin and/or β-glucan, among them, methods utilizing chromophore or fluorescent group which greatly changes intensity of color or fluorescence by cleaving amide bond lying adjacent to the chromophore or the fluorescent group, namely, methods for determination using synthetic peptide derivatives, in which a chromophore compound or a fluorescent compound such as nitrophenol, nitroaniline, coumarin derivative and indoxyl derivative is introduced through amide bond, as a substrate for endotoxin measurement have been reported (Patent Literature 1, Patent Literature 2, Patent Literature 3, Patent Literature 4). However, in each case of the determination methods employing such substrates, a chromophore or a fluorescent group which changes intensity of color or fluorescence by cleaving amide bond lying just adjacent to the chromophore group or the fluorescent group has been introduced. As a result, these methods had a problem of not applicable to highly sensitive determination due to the reasons such as low sensitivity of determination, and influence of interfering substances in the serum being unavoidable because excitation wavelength of the released substance was in a range of that possessed by the interfering substances.

Patent Literature 1: JP-B-59-19532
Patent Literature 2: JP-B-61-54400
Patent Literature 3: JP-A-57-502266
Patent Literature 4: JP-A-8-34796

DISCLOSURE OF INVENTION

Problem to be Solved by the Invention

An object of the present invention is to provide a peptide derivative for determining β-glucan or endotoxin which allows high sensitivity measurement, and a method for determining β-glucan and/or endotoxin using the peptide derivative.

Means for Solving Problem

In view of the above described situation, and taking notice that a method by which separation based on molecular weight difference is performed in a short time using a compact equipment (for example, capillary chip electrophoresis and the like) has been developed in recent years, the present inventors considered that if said method was utilized, a chromophore or a fluorescent group other than the conventional chromophore or fluorescent group which greatly changed intensity of color or fluorescence as a result of cleavage of the amide bond lying adjacent to the chromophore or fluorescent group could be applicable. Therefore, studies were made by considering that if a substrate in which a fluorescent dye having an excitation wavelength longer than those possessed by interfering substances in the serum (300 to 450 nm) had been introduced was utilized, the determination of β-glucan and/or endotoxin in high sensitivity would be possible. However, when such dye was introduced into the conventionally used substrate (for example, X-F-Gly-Arg-Y, wherein X-F- represents an amino acid residue in which N-terminal was protected; Gly represents glycine residue; Arg represents arginine residue; and Y represents chromophore or fluorescent group which greatly changes intensity of color or fluorescence by releasing) instead of Y, it was found that there was a problem that reactivity with clotting enzyme which had been activated through a cascade of an amebocyte lysate of a horseshoe crab such as LAL (Limulus amebocyte lysate) was low (delay in reactivity with the enzyme). And so, further investigation was made, and it was found that by introducing one more amino acid residue into the C-terminal of X-F-A-Gly-Arg-, and introducing the above dye thereto, the substrate could be cleaved specifically by the clotting enzyme, and the reaction rate was equal to or higher than that of the conventional substrates. That is, it was found that a peptide derivative represented by the following general formula [1]:

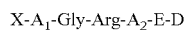  [1]

(wherein, X represents an N-terminal protecting group of amino acid, $A_1$ represents an amino acid residue or a peptide residue constituted with 2 to 3 amino acid residues, Gly represents a glycine residue, Arg represents an arginine residue, $A_2$ represents a glycine residue, a lysine residue, a threonine residue, an asparagine residue, or an alanine residue, E represents a spacer or a binding arm and D represents a substituent derived from fluorescent dye, respectively); was cleaved specifically at the bond between Arg and $A_2$ by clotting enzyme, and further the reaction rate of the clotting enzyme with the peptide is equal to or higher than that with the conventional substrates, thus the present invention was completed.

The present invention relates to (1) a peptide derivative represented by the following general formula [1]:

X-A$_1$-Gly-Arg-A$_2$-E-D  [1]

(wherein, X, A$_1$, Gly, Arg, A$_2$, E and D are the same as described above);
(2) a reagent for determining β-glucan and/or endotoxin, comprising the above-described peptide derivative; (3) a method for determining β-glucan and/or endotoxin, characterized in that a sample containing β-glucan and/or endotoxin, an amebocyte lysate of a horseshoe crab and the above-described peptide derivative are reacted each other, then the resulting released compound represented by the following general formula [2]:

H-A$_2$-E-D  [2]

(wherein, A$_2$, E, and D are same as described above); is separated from unreacted substance and quantified, and the determination is made based on this value; and (4) a reagent kit for determining β-glucan and/or endotoxin, comprising an amebocyte lysate of a horseshoe crab and the above-described peptide derivative as constituents thereof.

Effect of the Invention

According to the present invention, β-glucan and/or endotoxin, particularly β-glucan and/or endotoxin in serum can be determined in high sensitivity as compared with the conventional methods. Moreover, determination in a short period of time can be made as compared with the conventional methods.

BEST MODE FOR CARRYING OUT THE INVENTION

Figure 1:
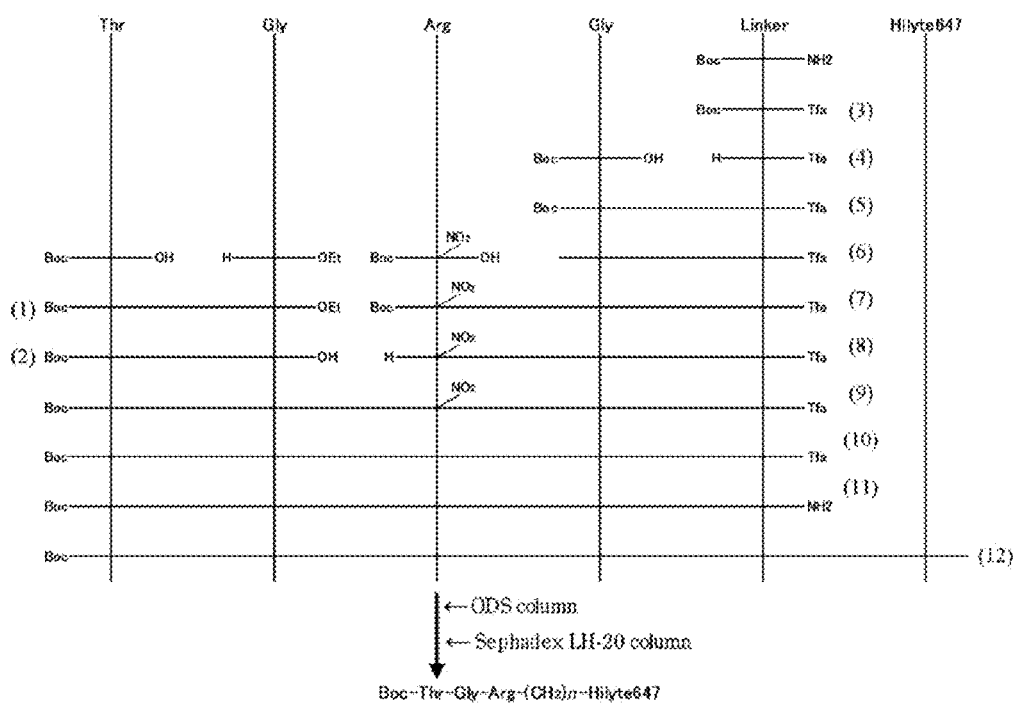
FIG. 1 shows a schematic diagram of the synthesis of Boc-Thr-Gly-Arg-Gly-NH(CH$_2$)$_4$NH-Hilyte647 using Boc-Thr-OH, H-Gly-OEt, Boc-Arg(NO$_2$)—OH, Boc-Gly-OH, Boc-NH-(CH$_2$)$_4$—NH$_2$, and Hilyte647 as starting materials. In addition, (1) to (12) in FIG. 1 represents the compounds (1) to (12) obtained by the syntheses (i) to (xii) of the Example 1, respectively.

The peptide derivative of the present invention is the one which is represented by the following general formula [1]:

X-A$_1$-Gly-Arg-A$_2$-E-D  [1]

(wherein, X, A$_1$, Gly, Arg, A$_2$, E and D are same as described above), and the peptide derivative represented by said general formula [1] may form acid addition salt with inorganic acid or organic acid, and specific example of such acid addition salt includes preferably, for example, inorganic acid salts such as hydrochloric acid salt, sulfuric acid salt, and nitric acid salt, and organic acid salts such as acetic acid salt, oxalic acid salt, tartaric acid salt, succinic acid salt, citric acid salt, and p-toluenesulphonic acid salt, and the like.

In the general formula [1], an N-terminal protecting group of amino acid represented by X is not particularly limited, so long as the protecting group is the one usually employed in this field as an N-terminal protecting group of amino acid or peptide, and includes, for example, acetyl group, benzoyl group, benzyloxycarbonyl group, tosyl group, glutaryl group, t-butoxycarbonyl group, and the like, and among them, t-butoxycarbonyl group and the like are preferable.

In the general formula [1], an amino acid residue represented by A$_1$ includes glycine residue, alanine residue, valine residue, leucine residue, isoleucine residue, serine residue, threonine residue, cystine residue, methionine residue, phenylalanine residue, tryptophan residue, tyrosine residue, proline residue, glutamic acid residue, aspartic acid residue, glutamine residue, asparagine residue, lysine residue, arginine residue, histidine residue, and the like, and among them, leucine residue, isoleucine residue, serine residue, threonine residue, and the like are preferable, leucine residue, serine residue, threonine residue, and the like are more preferable, and threonine residues is particularly preferable. In addition, a peptide residue represented by A$_1$ which consists of two to three amino acid residues may be the one which is usually employed in this field and not cleaved by clotting enzyme includes, for example, dipeptide residue such as valyl-leucine residue, leucyl-leucine residue, isoleucyl-leucine residue, valyl-serine residue, valyl-threonine residue, etc., or tripeptide such as residue, glycyl-valyl-serine residue, glycyl-valyl-threonine residue, and the like, and among them, valyl-leucine residue, valyl-threonine residue, glycyl-valyl-serine residue, glycyl-valyl-threonine residue, and the like are preferable, and valyl-threonine residue, glycyl-valyl-threonine residue, and the like are more preferable. In the specific examples of the above-described A$_1$, leucine residue, isoleucine residue, serine residue, threonine residue, valyl-threonine residue, glycyl-valyl-threonine residue, and the like are preferable, and among them, amino acid residue such as leucine residue, isoleucine residue, serine residue, threonine residue, and the like are preferable, leucine residue, serine residue, threonine residue, and the like are more preferable, and threonine residues is particularly preferable.

$A_2$ in the general formula [1] includes glycine residue, lysine residue, threonine residue, asparagine residue or alanine residue, and among them, glycine residue is preferable.

As to the binding arm or the spacer represented by E in the general formula [1], when a functional group possessed by a fluorescent dye which is an origin of the fluorescent dye-derived substituent represented by D (hereinafter, sometimes abbreviated simply as "functional group in the original fluorescent dye") is capable of binding easily to a terminal carboxylic acid of amino acid represented by $A_2$-OH, E represents a binding arm; and when the functional group in the original fluorescent dye is not capable of binding to the terminal carboxylic acid of amino acid represented by $A_2$-OH, E represents a spacer derived from a compound which has a reactive group in one side capable of binding easily to a terminal carboxylic acid of amino acid represented by $A_2$-OH and has a reactive group in other side capable of binding easily to the functional group in the original fluorescent dye. The original compound of such spacer includes a compound represented by the following general formula [3]:

$$R_1\text{-}A\text{-}R_2 \quad [3]$$

[wherein, $R_1$ represents a group having reactivity with carboxyl group (hereinafter, sometimes abbreviated as "reactive group represented by $R_1$"), A represents a straight-chain alkylene group having 1 to 6 carbon atoms, $R_2$ represents a group having reactivity with the functional group in the fluorescent dye which is an original of the substituent represented by D (hereinafter, sometimes abbreviated as "reactive group represented by $R_2$"), respectively].

The reactive group represented by $R_1$ in the general formula [3] may be a group which has reactivity with carboxyl group of amino acids (glycine residue, lysine residue, threonine residue, asparagine residue or alanine residue) represented by $A_2$, and includes, for example, amino group, hydroxyl group, thiol group, and the like.

The straight-chain alkylene group having 1 to 6 carbon atoms represented by A in the general formula [3] includes, for example, methylene group, ethylene group, n-propylene group, n-butylene group, n-pentylene group, n-hexylene group and so on.

The reactive group represented by $R_2$ is not particularly limited, so long as the group is capable of binding to functional group in the original fluorescent dye of the substituent represented by D (for example, amino group, carboxyl group, thiol group, hydroxyl group, maleimide group and the like; hereinafter, sometimes abbreviated as "functional group of dye-derived substituent"), and includes all groups usually employed in this field, for example, amino group, hydroxyl group, thiol group, maleimide group, a group represented by the following general formula [4]:

$$-\text{COOR}_3 \quad [4]$$

(wherein, $R_3$ represents hydrogen atom, alkaline metal atom, organic ammonium ion or ammonium ion), and includes —COO⁻ as preferable one, and these are selected appropriately according to the functional group in the original fluorescent dye.

In the general formula [4], the alkaline metal atom represented by $R_3$ includes, for example, lithium atom, sodium atom, potassium atom, rubidium atom, and the like, among them, sodium atom or potassium atom is preferable, and sodium atom is more preferable.

In the general formula [4], the organic ammonium ion represented by $R_3$ includes, for example, trialkyl ammonium ion and the like. Such trialkyl ammonium ion may be any one of straight-chain, branched or cyclic structure, and includes usually the one having 1 to 10 carbon atoms, preferably 1 to 6 carbon atoms. Specifically the organic ammonium ion includes, for example, trimethylammonium ion, triethylammonium ion, tri-n-propylammonium ion, triisopropylammonium ion, tributylammonium ion, tripentylammonium ion, trihexylammonium ion, triheptylammonium ion, trioctylammonium ion, trinonylammonium ion, tridecylammonium ion, tricyclopropylammonium ion, ion, tricyclopentylammonium ion, tricyclohexylammonium ion, tricycloheptylammonium ion, tricyclooctylammonium ion, tricyclononylammonium ion, tricyclodecylammonium ion and the like, and among them, trimethylammonium ion or triethylammonium ion is preferable, and triethylammonium ion is more preferable.

In the specific examples of $R_3$ in the above-described general formula [4], alkaline metal atom such as sodium atom and potassium atom; hydrogen atom; triethylammonium ion, and the like are preferable, and among them, sodium atom, hydrogen atom, and the like are preferable.

In order to facilitate the reaction of the reactive group represented by $R_2$ in the general formula [3] with the original functional group (for example, amino group, carboxyl group, thiol group, hydroxyl group, maleimide group, and the like) in the fluorescent dye of the substituent represented by D, a suitable reaction activating group (hereinafter, sometimes abbreviated as "reaction activating group of $R_2$") may be introduced to react with said functional group by reacting with a suitable compound. As described above, a group in which the reaction activating group has been introduced into the reactive group represented by $R_2$ (namely, -reactive group-reaction activating group) is also included in the "reactive group represented by $R_2$".

The reaction activating group of $R_2$ is not particularly limited, so long as it can be bound to the functional group in the original fluorescent dye of the substituent represented by D and can activate reactivity between said functional group and reactive group, and all groups usually used in this field are included. Specifically, for example, when the functional group in the original fluorescent dye of the substituent represented by D is amino group, succinimide group, sulfosuccinimide group, norbornene group, 4-nitrophenoxy group, a group derived from carboxylic acid anhydride (for example, acetoxycarbonylmethyl group, propyonyloxy carbonylethyl group, benzoyloxybenzyl group, and the like), isothiocyanate group, isocyanate group, monohalogen, phosphoryl halide, and the like are included; and when the functional group in the original fluorescent dye of the substituent represented by D is thiol group, for example, carboxylic acid anhydride, maleimide group, 2-pyridyldithio group, and the like are included. In addition, when the functional group in the original fluorescent dye of the substituent represented by D is hydroxyl group, the reaction activating group includes, for example, carboxylic acid anhydride, halosulfonylalkyl group having to 3 carbon atoms, halosulfonylaryl group, phosphamidite group, halocarbonylalkyl group having 1 to 3 carbon atoms, halocarbonylaryl group, isothiocyanate group, isocyanate group, phosphoryl halide, and the like; when the functional group in the original fluorescent dye of the substituent represented by D is carboxyl group, for example, amino group, hydroxyl group, thiol group, and the like are included; and when the functional group in the original fluorescent dye of the substituent represented by D is maleimide group, thiol group, and the like, are included.

In addition, it is possible to bind the dye-derived substituent to the spacer by introducing the reaction activating group into the above-described functional group in the original fluorescent dye of the substituent represented by D, and then reacting the reaction activating group with the reactive group of $R_2$. In this case, as the reaction activating group which is bound to the functional group in the original fluorescent dye of the substituent represented by D, the reaction activating group as described above is employed depending on the type of reactive group of $R_2$.

A preferable specific example of the compound represented by the general formula [3] includes, for example, $NH_2$—$(CH_2)_4$—$NH_2$, $NH_2$—$(CH_2)_3$—$NH_2$, and $NH_2$—$(CH_2)_2$—$NH_2$, and the like.

In the peptide derivative represented by the general formula [1], the fluorescent dye-derived substituent represented by D may be any substituent, so long as it is the one derived from the dye which is usually employed in this field, but those having an excitation wavelength of 500 to 800 nm is preferable, and among them, those having an excitation wavelength of 600 to 800 nm is more preferable. When the excitation wavelength of the dye is within the above-described range, influence of components other than the measuring object contained in the serum is avoidable, and therefore, high sensitivity measurement becomes possible. In addition, regarding the above-described dye, the one having molar absorbance coefficient of 100,000 to 500,000 at the maximum absorption wavelength is preferable, and the one having that of 100,000 to 300,000 is more preferable. In addition, said molar absorption coefficient means a value measured by the method usually used in this field. For example, the molar absorption coefficient represents a value which is obtained by measuring an absorbance of a sample dye solution with known concentration according to the common procedure using a spectrophotometer, and calculating by the following equation:

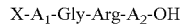

[$\epsilon$; molar absorption coefficient, c; sample concentration (mol/L), l; light path length (cm), $I_0$; intensity of incident light, I; intensity of light after passing and absorbing through the sample.]

A preferable specific example of the fluorescent dye in the fluorescent dye-derived substituent represented by D includes, for example, cyanine dye. The cyanine dye mentioned here is a compound in which two heterocycles are bound together by a methine group or a polymethine group, and at least one heterocycle of said heterocycles is nitrogen-containing heterocycl, and the one in which both of the heterocycles are nitrogen-containing heterocycle is preferable. As the substituent derived from the above-described cyanine dye, for example, the one derived from Cy-type dye described in U.S. Pat. No. 4,981,977, U.S. Pat. No. 5,268,486, U.S. Pat. No. 5,486,616 and so on, the one derived from Dy-type dye described in U.S. Pat. No. 6,083,485 and so on, the one derived from HiLyte-type dye described in WO 2006/047452 and so on, and the one derived from Alexa-type dye and the like are preferable. In addition, substituents derived from commercially available dyes may be used, and for example, the case where the substituent derived from Cy-type dye is utilized includes the one derived from Cy3, Cy3.5, Cy5, Cy5.5, Cy7 and so on (these are all product names of Amersham Bioscience); the case where the substituent derived from Dy-type dye includes the one derived from DY-700, DY-701, DY-730, DY-731, DY-732, DY-734, DY-750, DY-751, DY-752, DY-776, DY-780, DY-781, DY-782 and so on; case where the substituent derived from HiLyte-type dye includes the one derived from HILYTE FLUOR™ 555 dye, HILYTE FLUOR™ 647 dye, HILYTE FLUOR™ 680 dye, HILYTE FLUOR™ 750 dye and so on (these are all product names of AnaSpec Inc.); the case where the substituent derived from Alexa-type dye includes the one derived from ALEXA FLUOR® 532 dye, ALEXA FLUOR® 546 dye, ALEXA FLUOR® 555 dye, ALEXA FLUOR® 568 dye, ALEXA FLUOR® 594 dye, ALEXA FLUOR® 633 dye, ALEXA FLUOR® 647 dye, ALEXA FLUOR® 660 dye, ALEXA FLUOR® 680 dye, ALEXA FLUOR® 700 dye, ALEXA FLUOR® 750 dye and so on (these are all product names of Molecular Probes Inc.), as a preferable one.

In the above-described fluorescent dye-derived substituent represented by D, the one derived from HiLyte-type dye is preferable. Specifically, the one derived from HILYTE FLUOR™ 555 dye, HILYTE FLUOR™ 647 dye, HILYTE FLUOR™ 680 dye, HILYTE FLUOR™ 750 dye and so on are preferable, and the one derived from HILYTE FLUOR™ 647 dye thereinafter "Hilyte647") is particularly preferable. In addition, when such dye has a group which is capable of reacting with a carboxyl group such as hydroxyl group, amino group, thiol group and the like, the dye can be directly bound to A2 without through spacer, and therefore E should be a binding arm; and when such dyes have only a group which has no reactivity with a carboxyl group, a spacer becomes necessary, and therefore E should be a spacer.

The peptide derivatives represented by the general formula [1] is not particularly limited, so long as X, $A_1$, A2, E, and D are each same as described above, but preferable examples include the followings:
Boc-Thr-Gly-Arg-Gly-NH($CH_2$)$_4$NH-Hilyte647;
Boc-Thr-Gly-Arg-Lys-NH($CH_2$)$_4$NH-Hilyte647;
Boc-Thr-Gly-Arg-Thr-NH($CH_2$)$_4$NH-Hilyte647;
Boc-Thr-Gly-Arg-Asn-NH($CH_2$)$_4$NH-Hilyte647;
Boc-Thr-Gly-Arg-Thr-NH($CH_2$)$_4$NH-Hilyte647;
Boc-Ser-Gly-Arg-Gly-NH($CH_2$)$_4$NH-Hilyte647; and
Boc-Leu-Gly-Arg-Gly-NH($CH_2$)$_4$NH-Hilyte647.

In this regard, in the above-described peptide derivatives, Boc represents t-butoxycarbonyl group, Thr represents threonine residue, Gly represents glycine residue, Arg represents arginine residue, Lys represents lysine residue, Asn represents asparagine, Ser represents serine residue, and -Hilyte647 represents the one in which the carboxyl group in Hilyte647 is bound with amino group by amide bond, respectively.

Production of the peptide derivative represented by the general formula [1] may be carried out according to the method commonly employed in the peptide synthesis. The synthesis is carried out, for example, as follows.

Namely, the peptide derivative is synthesized by preparing a peptide derivative represented by the following general formula [6]:

$$X\text{-}A_1\text{-Gly-Arg-}A_2\text{-OH} \qquad [6]$$

(wherein, X, $A_1$, Gly, Arg and $A_2$ are same as described above);
then introducing a dye-derived substituent which may have a spacer represented by -E-D of the above-described general formula [1] into said peptide derivative.

As to the synthesis method for the peptide derivative represented by the general formula [6], each amino acid residue of Gly and Arg, and peptide residue or amino acid residue represented by $A_1$ and $A_2$ may be bound together so as to be in the order corresponding to the above-described general formula [6] according to the method usually used in this field. And the binding order may be either of binding Gly, Arg and $A_2$ sequentially to $A_1$ having N-terminal protecting group, or binding a combined substance of Arg and $A_2$ to a combined substance of $A_1$ having N-terminal protecting group and Gly, and the synthesis may be carried out by the method selected by easiness of handling or height of recovery rate as appropriate. As a preferable method, for example, the method for obtaining the peptide derivative of the general formula [6] by binding a combined substance of Arg and $A_2$ to a combined substance of $A_1$ having N-terminal protecting group and Gly is described below.

That is, firstly, an amino acid residue or a peptide residue composed of 2 to 3 amino acid residues which is represented by $A_1$ having N-terminal protecting group is bound to glycine to synthesize the peptide derivative represented by the following general formula [7]:

$$X\text{-}A_1\text{-}Gly\text{-}OH \qquad [7]$$

(wherein, X, $A_1$ and Gly are same as described above).

Specifically, for example, glycine in which carboxyl group has been protected by a protecting group such as methoxycarbonyl group and ethoxycarbonyl group is reacted with 1 to 2 equivalents to glycine of X-$A_1$-OH derived from an amino acid residue or a peptide residue composed of 2 to 3 amino acid residues represented by the above-described $A_1$, in which amino group is protected by a suitable protecting group such as t-butoxycarbonyl group and benzyloxycarbonyl group, in a solvent usually used in the synthesis of peptide derivative, for example, dimethylformamide (DMF), tetrahydrofuran (THF), dichloromethane or a mixed solvent thereof, under the presence of 1 to 2 molar quantity to glycine of a condensing agent commonly used in the peptide synthesis, for example, dicyclohexylcarbodiimide (DCC), at 0 to 25° C. for 12 to 24 hours. After the completion of the reaction, the reaction solution is concentrated under the reduced pressure, then subjected to a method usually used for purification of peptide derivatives, for example, crystallization in organic solvent such as hexane, or purification by silica gel column chromatography, ion-exchange column chromatography and the like, and thereby, the glycine derivative represented by the following general formula [8]:

$$X\text{-}A_1\text{-}Gly\text{-}Z \qquad [8]$$

(wherein, Z represents C-terminal protecting group such as methoxycarbonyl group and ethoxycarbonyl group, and X, $A_1$, and Gly are same as described above);
is obtained.

In addition, the glycine derivative represented by the general formula [8] may be synthesized by the method widely used in the field of peptide chemistry other than the above-described method, for example, active ester method, mixed acid anhydride method, azide method, phosphazo method, and the like. With respect to the synthetic method which will be explained below, it may also be carried out by the method widely used in this field other than the method described specifically.

Then, after the resulting glycine derivative represented by the general formula [8] is dissolved, for example, in a solvent such as methanol, the solution is reacted by adding a strong base such as sodium hydroxide to eliminate the C-terminal protecting group represented by Z, neutralized with a strong acid such as hydrochloric acid, and extracted with a suitable solvent such as ethyl acetate and n-butanol, to obtain the peptide derivative represented by the general formula [7].

Subsequently, arginine and the amino acid represented by $A_2$ are bound to synthesize the peptide derivative represented by the following general formula [9]:

$$H\text{-}Arg\text{-}A_2\text{-}Z \qquad [9]$$

(wherein, Arg, $A_2$, and Z are same as described above).
Specifically, the synthesis may be carried out, for example, as follows.

Namely, an amino acid represented by H-$A_2$-Z derived from $A_2$ in which carboxyl group has been protected by a protecting group such as methoxycarbonyl group and ethoxycarbonyl group is reacted with 1 to 2 equivalents to said amino acid of arginine in which amino group or both amino group and guanidino group have been protected by a suitable protecting group such as t-butoxycarbonyl group and benzyloxycarbonyl group, in a solvent usually used in the synthesis of peptide derivative, for example, dimethylformamide (DMF), tetrahydrofuran (THF), dichloromethane or a mixed solvent thereof, under the presence of 1 to 2 molar quantity to arginine of a condensing agent commonly used in the peptide synthesis, for example, dicyclohexylcarbodiimide (DCC), at 0 to 25° C. for 12 to 24 hours. After the completion of the reaction, the reaction solution is concentrated under the reduced pressure, then subjected to a method usually used for purification of peptide derivatives, for example, crystallization in organic solvent such as hexane, or purification by silica gel column chromatography, ion-exchange column chromatography and the like, to obtain the arginine derivative represented by the following general formula [10]:

$$X\text{-}Arg\text{-}A_2\text{-}Z \qquad [10]$$

(X, Arg, $A_2$, and Z are same as described above).

The obtained arginine derivative represented by the general formula [10] is further dissolved, for example, in a solvent such as dioxane, and the solution is reacted by adding a strong acid solution such as hydrochloric acid to eliminate the N-terminal protecting group represented by X, and then extracted with a suitable solvent such as ethyl acetate, to obtain the peptide derivative represented by the general formula [9].

By reacting both of the peptide derivatives represented by the general formulas [7] and [9] obtained as described above in a solvent under the presence of a condensing agent, concentrating under the reduced pressure, and purifying in the same way as in the synthesis of the peptide derivatives represented by the above-described general formulas [7] and [9], and further reacting with a strong base to eliminate C-terminal protecting group in the same way as in the synthesis of the peptide derivative represented by the general formula [7] from the glycine derivative represented by the general formula [8], the compound represented by the above-described general formula [6] can be obtained easily yet in high yield.

By binding the dye-derived substituent (-E-D group) which may have a spacer to the thus obtained peptide derivative represented by the general formula [6], the peptide derivative represented by the above-described general formula [1] is obtained. As to the method, for example, using a dye compound represented by $R_5$-D' ($R_5$ represents a functional group in the dye; D' represents a structure excluding the functional group from the dye compound), for example, when $R_5$ is an amino group or a hydroxyl group, the dye compound may be reacted with the carboxyl group located in the C-terminal side of the peptide derivative to be introduced according to a common method. In addition, when $R_5$ is a carboxyl group, the binding may be carried out according to the method usually used in this field. For example, a spacer (for example, a diamine compound) is bound to $R_5$-D' to synthesize $R_1$-A-$R'_2$-D (in this regard however, $R_1$, A, and D are same as described above; $R'_2$ represents a divalent group which has reactivity to the functional group in the substituent derived from fluorescent dye represented by D; for example, $H_2N$-A-NH-D), which is then reacted with carboxyl group in the C-terminal side of the peptide derivative, or after binding a spacer to carbonyl group in the C-terminal side of the peptide derivative, $R_5$-D' is bound to said spacer. Also, when purification is required, it may be carried out as appropriate according to the purification method usually used in this field.

Furthermore, when a reaction activating group is used on introducing spacer, the reaction may be carried out in the same way as described above after introducing the reaction activating group into the reactive group represented by $R_1$ or/and $R_2$ by the method usually employed. For example, when the reaction activating group is introduced into both $R_1$ and $R_2$ of the spacer, the introduction may be carried out as follow. For example, the carboxyl group located in the C-terminal side of the peptide derivative is reacted with the reactive group represented by $R_1$ in which the reaction activating group has been introduced to combine the peptide derivative and the spacer, subsequently the reactive group represented by $R_2$ in which the reaction activating group has been introduced is bound to the functional group ($-R_5$) of the dye-derived substituent to combine the spacer bound to the peptide derivative and the dye-derived substituent. In addition, the reaction activating group may be introduced into the functional group of dye-derived substituent, and in that case, in the same way as described above, the functional group ($-R_5$) of the dye-derived substituent in which the reaction activating group has been introduced may be bound to the reactive group represented by $R_2$.

The method for binding the dye-derived substituent which may have a spacer (-E-D group) to the peptide derivative represented by the general formula [6] is carried out specifically as follows. That is, for example, the peptide derivative represented by the general formula [6] is reacted with 1-2 molar quantity to said peptide derivative of dye compound which may have a spacer (for example, a compound represented by $R_5$-D' or $H_2N$-A-$R'_2$-D, in this regard however, $R_5$, D', A, $R'_2$, and D are same as described above) in a solvent usually used in the synthesis of peptide derivative, for example, dimethylformamide (DMF), dimethylsulfoxide (DMSO), tetrahydrofuran (THF) or a mixed solvent thereof, under the presence of 1 to 2 molar quantity to the peptide derivative represented in the general formula [6] of condensing agent commonly used in the peptide synthesis, for example, dicyclohexylcarbodiimide (DCC), at 0 to 25° C. for 12 to 24 hours. After the completion of the reaction, the reaction solution is concentrated under the reduced pressure, and then the product is purified by a method usually used for purification of peptide derivatives, for example, by crystallization from an organic solvent such as hexane, or by silica gel column chromatography, ion-exchange column chromatography and the like, to obtain the peptide derivative represented by the general formula [1].

In addition, when the dye-derived substituent is bound to the peptide derivative represented by the general formula [6] through a spacer, the dye compound having spacer as described above may be used for the reaction, and the peptide derivative represented by the general formula [6] in which a spacer has been bound to $A_2$ may be used to bind to the dye-derived substituent. In addition, the peptide derivative represented by the general formula [6] having a spacer may be synthesized, by binding a spacer to $A_2$ in the peptide derivative represented by the general formula [9], or the peptide derivative represented by the general formula [6] having a spacer may be synthesized via the peptide derivative represented by the general formula [9] having a spacer, by binding a spacer to $A_2$ before preparing the peptide derivative represented by the general formula [9] in advance. In order to reduce a risk of by-product formation, it is preferable to bind a spacer to $A_2$ in advance, and the method may be carried out, for example, as described below. That is, for example, when butanediamine residue is used as a spacer, by subjecting butanediamine in which either one of amino groups has been protected by a protecting group such as, for example, trifluoromethylcarbonyl group and an amino acid derivative represented by the following general formula [11]:

$$X\text{-}A_2\text{-}OH \qquad [11]$$

(wherein, X and $A_2$ are same as described above);
in which the amino group has been protected by an appropriate protecting group such as t-butoxycarbonyl group, benzyloxycarbonyl group, to condensation reaction, concentration under the reduced pressure, and purification procedure in the same way as in the preparation method described in the above general formulas [7] and [9], an amino acid derivative represented by the following general formula [12]:

$$X\text{-}A_2\text{-}E\text{-}Tfa \qquad [12]$$

(wherein, E represents butanediamine residue, and Tfa represents trifluoromethylcarbonyl group; X and $A_2$ are same as described above); can be obtained. By reacting the resulting amino acid derivative represented by the general formula [12] by adding strong acid solution such as hydrochloric acid and eliminating the N-terminal protecting group represented by X, in the same way as in the method for obtaining the peptide derivative represented by the general formula [9] from the above described peptide derivative represented by the general formula [10], $A_2$ in which butandiamine residue (spacer) is bound can be obtained. By carrying out the synthesis using $A_2$ in which said spacer is bound in the same way as in the method described above, the peptide derivative represented by the general formula [9] having a spacer can be obtained; the peptide derivative represented by the general formula [6] having a spacer can be obtained; and the peptide derivative represented by the general formula [1] can be obtained.

Although the peptide derivative of the present invention obtained as described above is useful in the high sensitivity measurement of β-glucan and/or endotoxin, the reagent of the present invention comprises the peptide derivative of the present invention. The concentration is usually 1 nM to 10 mM, preferably 10 nM to 1 mM. In addition, said reagent may comprise the amebocyte lysate of the horseshoe crab. It should be noted that the amebocyte lysate of the horseshoe crab may be used without being limited particularly so long as it can be used for the usual β-glucan and/or endotoxin measurement, and the one which is prepared from commercially available freeze-dried products of an amebocyte lysate of a horseshoe crab manufactured by ACC Inc., Haemachem Inc., Lonza, Charles River Endosafe and so on may also be used, and the one which is obtained from the blood cell of the a horseshoe crab belonging to Limulus genus, Tachypleus genus, or Carcinoscorpius genus, and generates activation of enzyme (protease etc.) by the reaction with endotoxin and/or β-glucan will be included without being limited particularly.

The reagent of the present invention may further comprise other suitable reagents usually employed in this field such as buffering agents and alkaline earth metal salts, etc., and these reagents may be used by selecting appropriately from those employed in the so called synthetic substrate method. The above-described buffering agent includes, specifically, buffer solutions usually employed in this field such as trishydroxylaminomethane buffer solution, phosphate buffer solution, borate buffer solution, Good's buffer solution, and the like. Although the concentration of said buffering agent in the reagent varies somewhat depending on buffering agent to be employed, it is usually 5 mM to 500 mM, preferably 20 mM to 200 mM. In addition, the peptide derivative of the present invention in the reagent may be a freeze-dried product.

The reagent kit for endotoxin and/or β-glucan assay consists of a reagent comprising the peptide derivative of the present invention and the above reagent comprising an amebocyte lysate of a horseshoe crab. When needed, reagents such as stabilizers which are usually employed in this field including sugar alcohol such as mannitol and sorbitol, sugars such as sucrose and trehalose, polysaccharide such as dextran, proteins such as bovine serum albumin and the like may be added, and the concentration thereof, etc. may be set according to the range usually used in this field. In addition, in the reagent comprising the peptide derivative of the present invention and the reagent comprising the amebocyte lysate of the horseshoe crab, buffering agents and alkaline earth metal salts, etc. which are described in the section of the reagent of the present invention may be employed, and the concentration thereof, etc. may be used in the same range as described above. The amebocyte lysate of the horseshoe crab in the reagent comprising the amebocyte lysate of a horseshoe crab includes the same ones as described in the section of the above described reagent. Furthermore, the kit may be in combination with standard endotoxin and/or standard β-glucan for obtaining a standard curve. For said standard endotoxin and standard β-glucan, an official standard endotoxin preparation such as USP Reference Standard Endotoxin and Japanese pharmacopoeia standard endotoxin preparation, commercially available standard endotoxin and β-glucan preparation manufactured by Seikagaku Corporation, Associates of Cape Cod, Inc. (ACC), Wako Pure Chemical Industries Ltd., and so on, or the one which is produced according to the method described in JP3652738 may be employed. In addition, the reagents in these reagent kits may be freeze-dried product.

The method for determining β-glucan and/or endotoxin may be performed according to the known synthetic substrate method, that is, a a sample containing β-glucan and/or endotoxin and the amebocyte lysate of the horseshoe crab and the peptide derivative of the present invention are mixed and reacted, then the resulting released compound represented by the following general formula [2]:

$$H-A_2-E-D \qquad [2]$$

(wherein, $A_2$, E, and D are same as described above);
is separated, and quantified, and the determination may be done based on the results. In addition, in the above-described reaction of a sample containing β-glucan and/or endotoxin and the amebocyte lysate of the horseshoe crab and the peptide derivative of the present invention, the sample containing β-glucan and/or endotoxin and the amebocyte lysate of the horseshoe crab may be mixed and reacted, before the peptide derivative of the present invention is added and reacted.

The concentration of the peptide derivative of the present invention in the above-described reaction varies depending on the setting of measurement range of endotoxin, however, it is usually 0.01 to 1000 μM, preferably 0.1 to 500 μM, and more preferably 0.2 to 200 μM. As to the amount to be used, the peptide derivative of the present invention is usually 10 to 1000 μL, preferably 50 to 500 μL, and the amebocyte lysate of the horseshoe crab is usually 10 to 1000 μL, preferably 50 to 500 μL for 100 μL of the sample containing β-glucan and/or endotoxin. In addition, the temperature at the time of reaction is 25 to 40° C., preferably 30 to 37° C., and reaction time is usually 5 to 60 minutes, preferably 5 to 30 minutes, more preferably 5 to 10 minutes. Although said reaction time is usually 5 to 60 minutes, according to the method for measuring β-glucan and/or endotoxin of the present invention, since the released compound represented by the general formula [2] can be measured in high sensitivity without being influenced by contaminating impurities and the compound can be detected even if the reaction time is short, the reaction time can be reduced. In addition, the separation of the compound represented by the general formula [2] described below may be carried out immediately after completion of the reaction, however, it is more preferable to terminate the reaction after completion of the reaction using a reaction stop solution, and said reaction stopping solution includes, for example, aqueous acid solution such as hydrochloric acid solution and acetic acid solution, protease inhibitor solution such as amidinophenyl benzoate hydrochloride, benzamidine hydrochloride, and surface active agent solution such as sodium dodecyl sulfate, and the like. Concentration of the reaction stop solution is not particularly limited, so long as it inhibits sufficiently the activity of the clotting enzyme generated as a result of interaction between β-glucan and/or endotoxin and an amebocyte lysate of a horseshoe crab, however, in the case of aqueous acid solution, the concentration after addition of the stop solution is usually 10 to 2000 mM, preferably 50 to 1000 mM; in the case of protease inhibitor solution, the concentration after addition of the stop solution is usually 0.001 to 100 mM, preferably 0.1 to 10 mM; in the case of surface active agent solution, the concentration after addition of the stop solution is usually 0.1 to 10%, preferably 0.5 to 5%. As to the amount of the stop solution to be used, 1 to 200 v/v %, preferably 10 to 100 v/v % for the total reaction volume may be added. The method for separating the compound represented by the general formula [2] includes column chromatography, liquid chromatography, gel electrophoresis, capillary electrophoresis, and capillary chip electrophoresis and so on, among them, methods by liquid chromatography, capillary electrophoresis, and capillary chip electrophoresis are preferable, and capillary chip electrophoresis method is particularly preferable from the viewpoint of sensitivity. In addition, the conditions of these separation methods may be carried out according to the known method, for example, capillary chip electrophoresis may be carried out according to the method described in WO 2007/027495 etc. Detection of the compound represented by the general formula [2] may be carried out by equipment such as differential refraction detector, fluorescence detector, UV detector and the like, but among them, UV detector and fluorescence detector are preferable, and fluorescence detector is more preferable.

As for the method for measuring β-glucan and/or endotoxin of the present invention, specifically, for example, when the separation is carried out by the capillary chip electrophoresis and detection is carried out by the fluorescence detector, the measurements of β-glucan and/or endotoxin of the present invention may be carried out as follows. That is, 50 μL of a sample containing β-glucan and/or endotoxin, 20 to 50 μL of a solution comprising the amebocyte lysate of the horseshoe crab and 20 to 50 μL of the peptide derivative of the present invention, which is usually 0.01 to 10 μM, preferably 0.01 to 1 μM, are mixed, and reacted for 5 to 30 minutes, preferably 5 to 15 minutes, while kept warm at 25 to 40° C. After that, the reaction is terminated by adding the reaction stop solution, for example, aqueous acid solution such as acetic acid and hydrochloric acid, protease inhibitor solution, surface active agent solution or the like, and the resulting final solution is separated by a suitable separation method, for example, capillary chip electrophoresis, and measured, for example, by fluorescence detector. The measured value obtained is fitted on a standard curve showing the relationship between the concentration of β-glucan and/or endotoxin and said measured value which has been prepared in advance using β-glucan and/or endotoxin solutions of known concentrations, and thereby the concentration of β-glucan and/or endotoxin in the sample can be obtained.

Hereinafter, the present invention will be further explained in detail by referring to the following Examples, Reference Examples, etc., but the scope of the present invention is by no means limited thereto.

EXAMPLES

Example 1

Synthesis of Boc-Thr-Gly-Arg-Gly-NH(CH$_2$)$_4$NH-Hilyte647

Boc-Thr-Gly-Arg-Gly-NH(CH$_2$)$_4$NH-Hilyte647 was synthesized using Boc-Thr-OH, H-Gly-OEt, Boc-Arg(NO$_2$)—OH, Boc-Gly-OH, Boc-NH-(CH$_2$)$_4$—NH$_2$, and Hilyte647 as starting materials. The schematic diagram is shown in FIG. 1. In addition, (1) to (12) in FIG. 1 represent the compounds (1) to (12) obtained by the syntheses of the following (i) to (xii).

(i) Synthesis of Boc-Thr-Gly-OEt

Boc-threonine (produced by Wako Pure Chemical Industries Ltd.) (11.0 g, 50 mmol) and glycine ethyl ester hydrochloride (produced by Wako Pure Chemical Industries Ltd.) (8.4 g, 60 mmol) were dissolved in dichloromethane (250 mL). After triethylamine (8.4 mL, 60 mmol), N,N'-dicyclohexylcarbodiimide (DCC, 12.4 g, 60 mmol) and hydroxybenzotriazole (9.2 g, 60 mmol) were further added thereto, the mixture was reacted at room temperature for overnight with stirring. After completion of the reaction, reaction mixture was filtered, and then the filtrate was extracted with ethyl acetate. The extract was concentrated under reduced pressure, and the product was crystallized from hexane, to obtain Boc-Thr-Gly-OEt (1) (13.0 g) (yield; 85.1%).

(ii) Synthesis of Boc-Thr-Gly-OH

The obtained compound (1) (10.0 g, 33 mmol) was dissolved in methanol (150 mL), and 1 N aqueous sodium hydroxide (33 mL, 33 mmol) was further added thereto, and then the mixture was reacted at room temperature for 3 hours with stirring. After completion of the reaction, the reaction solution was neutralized with 1 N hydrochloric acid, and objective substance was extracted with a mixed solvent of ethyl acetate and n-butanol (mixing ratio=7:3). The extracted objective substance was concentrated under reduced pressure and dried, to obtain Boc-Thr-Gly-OH (2) (5.4 g) (yield; 60.2%).

(iii) Synthesis of Boc-NH-(CH$_2$)$_4$—NH-Tfa

N-Boc-butanediamine (produced by Tokyo Chemical Industry Co., Ltd.) (5.0 g, 27 mmol) was dissolved in chloroform (50 mL), and Methyl trifluoroacetate (25 g, 195 mmol) was added thereto, and then the mixture was reacted at room temperature for overnight with stirring. After completion of the reaction, the reaction solution was washed with H$_2$O, and the product was crystallized from hexane, to obtain N-Boc-N'-Tfa-butanediamine (3) (7.5 g) (yield; 99.3%).

(iv) Synthesis of H$_2$N-(CH$_2$)$_4$—NH-Tfa

The obtained compound (3) (7.3 g) was dissolved in 4 N hydrochloric acid/dioxane solution (50 mL), and the solution was reacted under ice-cooled condition for 3 hours with stirring. After completion of the reaction, diethyl ether was added thereto, and deposited crystal was collected by filtration, to obtain N-Tfa-butanediamine (4) (5.4 g) (yield; 96.8%).

(v) Synthesis of Boc-Gly-NH(CH$_2$)$_4$NHTfa

The obtained compound (4) (2.2 g, 10 mmol) and Boc-glycine (produced by Wako Pure Chemical Industries Ltd.) (1.6 g, 9.1 mmol) were dissolved in DMF (30 mL), and triethylamine (1.4 mL, 10 mmol), DCC (2.5 g, 12 mmol), and hydroxybenzotriazole (1.9 g, 12 mmol) were further added thereto, and then the mixture was reacted at room temperature for overnight with stirring. After completion of the reaction, reaction mixture were filtered, and the filtrate was extracted with ethyl acetate. The residue was purified by silica gel column, to obtain Boc-Gly-NH(CH$_2$)$_4$NHTfa (5) (3.2 g).

(vi) Synthesis of H-Gly-NH(CH$_2$)$_4$NHTfa

The obtained compound (5) (3.0 g, 8.8 mmol) was dissolved in 4 N hydrochloric acid/dioxane solution (50 mL), and the solution was reacted under ice-cooled condition for 3 hours with stirring. After completion of the reaction, diethyl ether was added thereto, and deposited crystal was collected by filtration, to obtain H-Gly-NH(CH$_2$)$_4$NHTfa (6) (2.4 g).

(vii) Synthesis of Boc-Arg(NO$_2$)-Gly-NH(CH$_2$)$_4$NHTfa

The obtained compound (6) (2.3 g, 8.3 mmol) and Boc-Arg(NO$_2$)—OH (produced by Wako Pure Chemical Industries Ltd.) (2.6 g, 8.1 mmol) were dissolved in DMF (30 mL), and triethylamine (1.1 mL, 8.3 mmol), DCC (1.7 g, 8.3 mmol) and hydroxybenzotriazole (1.3 g, 8.3 mmol) were further added thereto, and the solution was reacted at room temperature for overnight with stirring. After completion of the reaction, reaction mixture was filtered, and the filtrate was extracted with ethyl acetate. The residue was purified by silica gel column, to obtain Boc-Arg(NO$_2$)-Gly-NH(CH$_2$)$_4$NHTfa (7) (3.7 g).

(viii) Synthesis of H-Arg(NO$_2$)-Gly-NH(CH$_2$)$_4$NHTfa:HCl

The obtained compound (7) (3.5 g, 6.5 mmol) was dissolved in 4 N hydrochloric acid/dioxane solution (40 mL), and the solution was reacted under ice-cooled condition for 3 hours with stirring. After completion of the reaction, diethyl ether was added thereto, and deposited crystal was collected by filtration. The resulting crude product was purified by silica gel column, to obtain H-Arg(NO$_2$)-Gly-NH(CH$_2$)$_4$NHTfa:HCl (8) (3.0 g) (yield; 98.1%).

(ix) Synthesis of Boc-Thr-Gly-Arg(NO$_2$)-Gly-NH(CH$_2$)$_4$NHTfa

The obtained compound (8) (1.35 g, 2.8 mmol) and Boc-Thr-Gly-OH (2) (650 mg, 2.4 mmol) were dissolved in DMF (20 mL), and triethylamine (0.4 mL, 2.9 mmol), DCC (580 mg, 2.8 mmol) and hydroxybenzotriazole (430 mg, 2.8 mmol) were added thereto under ice-cooled condition, and the solution was reacted at room temperature for overnight with stirring. After completion of the reaction, reaction mixture was filtered, and the filtrate was extracted with ethyl acetate/n-butanol (6/1). After removing the solvent by evaporation, the residue was purified by silica gel column, to obtain Boc-Thr-Gly-Arg(NO$_2$)-Gly-NH(CH$_2$)$_4$NHTfa (9) (1.0 g) (yield; 63.0%).

(x) Synthesis of Boc-Thr-Gly-Arg-Gly-NH(CH$_2$)$_4$NHTfa

After dissolving compound (9) (1.0 g, 1.4 mmol) in methanol (50 mL) and adding palladium carbon (1.3 g) thereto, the mixture was reacted under hydrogen atmosphere at room temperature for 4 days with stirring. After completion of the reaction, palladium carbon was filtered off, and the filtrate was concentrated under reduced pressure. The residue was purified by silica gel column, to obtain Boc-Thr-Gly-Arg-Gly-NH(CH$_2$)$_4$NHTfa (10) (160 mg) (yield; 17.1%). As a result of analysis of this product by MS spectrum, a peak corresponding to the objective substance was confirmed (M$^-$=656.3).

(xi) Synthesis of Boc-Thr-Gly-Arg-Gly-NH(CH$_2$)$_4$NH$_2$

After dissolving the obtained compound (10) (150 mg, 0.22 mmol) in methanol (5 mL) and adding 25% aqueous ammonia (5 mL) thereto, the solution was reacted at room temperature for 3 hours with stirring. After completion of the reaction, the reaction solution was concentrated under reduced pressure. The residue was purified by silica gel column, then lyophilized, to obtain Boc-Thr-Gly-Arg-Gly-NH(CH$_2$)$_4$NH$_2$ (11) (26 mg) (yield; 20.3%). As a result of analysis of this product by MS spectrum, a peak corresponding to the objective substance was confirmed (M$^+$=560.3).

(xii) Synthesis of Boc-Thr-Gly-Arg-Gly-NH(CH$_2$)$_4$NH-Hilyte647

After dissolving the obtained compound (11) (8.0 mg, 14 µmol) in DMF (0.5 mL) and further adding triethylamine (4.0 µL, 28 µmol) and 4 mg (4 µmol) of Hilyte647-OSE (produced by AnaSpec Inc.) thereto, the solution was reacted at room temperature for overnight with stirring. After completion of the reaction, the reaction solution was concentrated under the reduced pressure, and the residue was purified by Wakosil 5C18 column (ODS column, produced by Wako Pure Chemical Industries Ltd.), then by Sephedex LH-20 (produced by Pharmacia Inc.). The residue was dissolved in water for injection, and filtered through a 0.2 µm membrane filter. The filtrate was lyophilized, to obtain Boc-Thr-Gly-Arg-Gly-NH(CH$_2$)$_4$NH-Hilyte647 (12) (2.6 mg).

Reference Example 1

Synthesis of Boc-Thr-Gly-Arg-NH(CH$_2$)$_4$NH-Hilyte647

Figure 2:
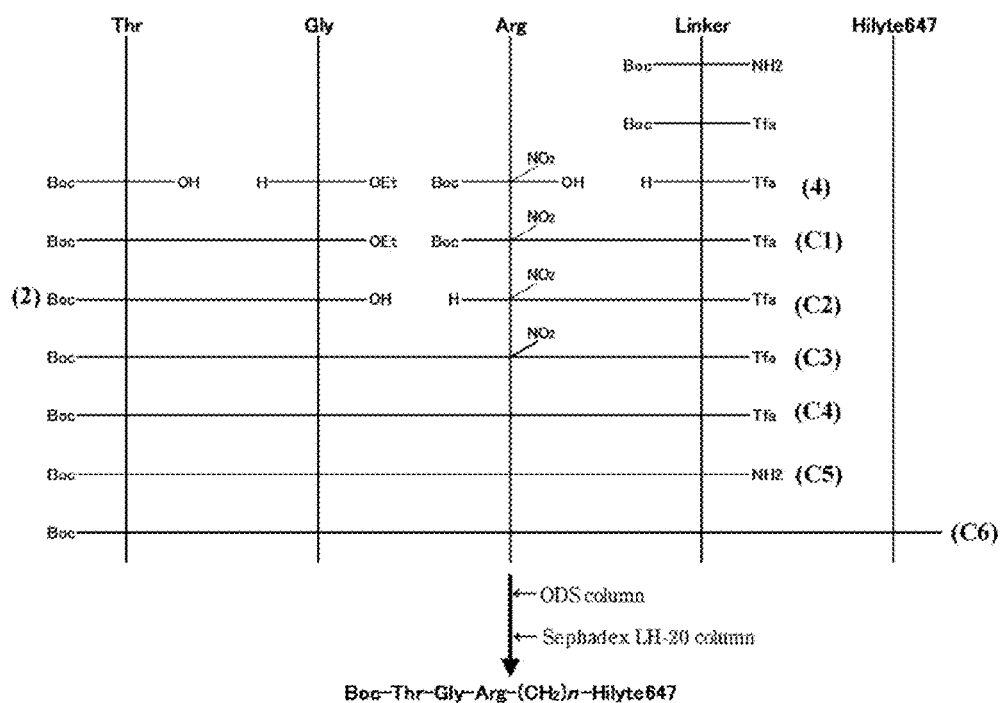
FIG. 2 shows a schematic diagram of the synthesis of Boc-Thr-Gly-Arg-NH(CH$_2$)$_4$NH-Hilyte647 using Boc-Thr-OH, H-Gly-OEt, Boc-Arg(NO$_2$)—OH, Boc-NH-(CH$_2$)$_4$—NH$_2$, and Hilyte647 as starting materials. In addition, (2) and (4) in FIG. 2 represent the compounds (2) and (4) obtained in (ii) and (iv) of Example 1, respectively, and (C1) to (C6) represent the compounds (C1) to (C6) obtained by the syntheses (i) to (vi) in the Reference Example 1, respectively.

Using Boc-Thr-OH, Gly-OEt, Boc-Arg(NO$_2$)—OH, Boc-NH-(CH$_2$)$_4$—NH$_2$, and Hilyte647 as starting materials, Boc-Thr-Gly-Arg-NH(CH$_2$)$_4$NH-Hilyte647 was synthesized. That is, the substance in which a fluorescent compound (or a chromophore group) in a known substrate was substituted by the "fluorescent dye-derived substituent involved in the present invention" was obtained. The schematic diagram is shown in FIG. 2. In addition, (2) and (4) in FIG. 2 represent the compounds (2) and (4) obtained in (ii) and (iv) of Example 1; (C1) to (C6) represent the compounds (C1) to (C6) obtained by syntheses in (i) to (vi) of the following Reference Example (i) to (vi), respectively.

(i) Synthesis of C-Terminal Peptide Unit

After dissolving Boc-Arg(NO$_2$)—OH (produced by Wako Pure Chemical Industries Ltd.) (3.0 g, 9.4 mmol) and N-Tfa-butanediamine (4) (2.2 g, 10 mmol) in DMF (40 mL) and further adding triethylamine (1.4 mL, 10 mmol), DCC (2.5 g, 12 mmol) and hydroxybenzotriazole (1.9 g, 12 mmol) thereto, the solution was reacted at room temperature for overnight with stirring. After completion of the reaction, reaction mixture was filtered, and the filtrate was extracted with ethyl acetate. By purifying the residue on a silica gel column, Boc-Arg(NO$_2$)—NH(CH$_2$)$_4$NHTfa (C1) (4.3 g) was obtained (yield; 95.2%).

(ii) Synthesis of C-Terminal Peptide Unit

The compound (C1) (4.0 g, 8.2 mmol) was dissolved in 4 N hydrochloric acid/dioxane solution (40 mL), and the solution was reacted under ice-cooled condition for 3 hours with stirring. After completion of the reaction, diethyl ether was added thereto, and deposited crystal was collected by filtration. By drying under the reduced pressure, H-Arg(NO$_2$)—NH(CH$_2$)$_4$NHTfa:HCl (C2) (3.47 g) was obtained (yield; 99.8%).

(iii) Synthesis of Tripeptide Unit

After dissolving the compound (C2) (1.2 g, 2.8 mmol) and Boc-Thr-Gly-OH (2) (650 mg, 2.4 mmol) in DMF (30 mL), and adding triethylamine (0.4 mL, 2.9 mmol), DCC (580 mg, 2.8 mmol), and hydroxybenzotriazole (430 mg, 2.8 mmol) thereto under ice-cooled condition, the mixture was reacted at room temperature for overnight with stirring. After completion of the reaction, reaction mixture was filtered, and the filtrate was extracted with ethyl acetate/n-butanol (6/1). After removing the solvent by evaporation, the residue was purified by silica gel column, to obtain Boc-Thr-Gly-Arg(NO$_2$)—NH(CH$_2$)$_4$NHTfa (C3) (660 mg) (yield; 43.7%).

(iv) Denitration Reaction

After dissolving the compound (C3) (600 mg, 0.9 mmol) in methanol (20 mL) and adding palladium carbon (500 mg) thereto, the mixture was react under hydrogen atmosphere at room temperature for 2 days with stirring. After completion of the reaction, reaction mixture was filtered, and the filtrate was concentrated under the reduced pressure. The residue was purified by silica gel column, to obtain Boc-Thr-Gly-Arg-NH(CH$_2$)$_4$NHTfa (C4) (530 mg) (yield; 95.0%). As a result of analysis of this product by MS spectrum, a peak corresponding to the objective substance was confirmed (M$^-$=599.3).

(v) Detrifluoroacetylation Reaction

After dissolving the compound (C4) (500 mg, 0.8 mmol) in methanol (10 mL) and adding 25% aqueous ammonia (10 mL) thereto, the solution was reacted at room temperature for 3 hours with stirring. After completion of the reaction, the reaction solution was concentrated under the reduced pressure, and the residue was purified by a silica gel column, and further lyophilized, to obtain Boc-Thr-Gly-Arg-NH(CH$_2$)$_4$NH$_2$ (C5) (330 mg) (yield; 78.6%). As a result of analysis of this product by MS spectrum, a peak corresponding to the objective substance was confirmed (M$^+$=503.2).

(vi) Fluorescent Labeling Reaction

After dissolving the compound (C5) (5.1 mg, 10 µmol) in DMF (0.5 mL) and further adding triethylamine (2.8 µL, 20 µmol) and 4 mg (4 µmol) of Hilyte647-OSE (produced by AnaSpec Inc.) thereto, the solution was reacted at room temperature for overnight with stirring. The reaction solution was concentrated under the reduced pressure, and the residue was purified by ODS column, then by Sephedex LH-20. The residue was dissolved in water for injection, and filtered through a 0.2 µm membrane filter. By lyophilizing the residue, Boc-Thr-Gly-Arg-NH(CH$_2$)$_4$NH-Hilyte647 (C6) (2.2 mg) was obtained.

Experimental Example 1

Study on the Reactivity of Clotting Enzyme by Substrate (i) Preparation of Various Kinds of Reagent Solutions a) β-glucan-free water: Japanese Pharmacopoeia Water for Injection (Otsuka Distilled Water, produced by Otsuka Pharmaceutical Factory, Inc.) was used.

b) Aqueous solution of the peptide derivative of the present invention (hereinafter, sometimes abbreviated as substrate of the present invention): Boc-Thr-Gly-Arg-Gly-NH(CH$_2$)$_4$NH-Hilyte647 was dissolved in β-glucan-free water, and prepared to give 640 µM.

c) Aqueous substrate solution of known analogous substrate: Boc-Thr-Gly-Arg-NH-(CH$_2$)$_4$—NH-HiLyte647 obtained in Reference Example 1 was dissolved in β-glucan-free water, and prepared to give 640 µM.

d) Standard β-glucan solution: Intravenous lentinan preparation "Astellas" (Astellas Pharma Inc.) (1 mg) was dissolved in 0.1 M aqueous sodium hydroxide to give 50 µg/mL, and the solution was then diluted appropriately with β-glucan-free water, and used as the standard β-glucan solution.

e) β-glucan specific LAL fraction solution: A fraction in which β-glucan-dependent clotting enzyme activity was detected was collected from the blood cell of American horseshoe crab (*Limulus polyphemus*) according to LAL extraction method described in pages 268 to 269 of "T. Kitagawa et al., Journal of Chromatography, 567 (1991) 267-273" and fractionation method by ion exchange chromatography, LAL fraction (a fraction corresponding to the fraction Nos. 7 to 20 in the above described literature) in 20 mM Tris-HCl buffer (pH 8.0) was obtained.

In addition, detection of the β-glucan-dependent clotting enzyme activity was performed as follows. Namely, a mixed solution which comprises the obtained fraction (25 volume), 1 M Tris-HCl buffer (pH 8.0) containing 1 M magnesium sulfate (5 volume), 10 mM t-Boc-Leu-Gly-Arg-p-nitroanilide aqueous solution (2 volume) and β-glucan-free water (18 volume) was mixed with the same volume of standard β-glucan solution or aqueous endotoxin solution (*Escherichia coli* O55: B5 strain-derived phenol extraction and purification product produced by Difco Laboratories Inc. was dissolved in water and diluted appropriately), and incubated at 37° C. for 30 minutes. Subsequently, after adding equal volume of 1 M acetic acid, absorbance at 405 nm was measured, and the β-glucan-dependent or endotoxin-dependent clotting enzyme activity was detected based on the results. As a result, the fraction, in which the endotoxin-dependent clotting enzyme activity is not detected for the endotoxin concentration range from 1 ng/mL to 100 μg/mL, however for β-glucan, β-glucan concentration-dependent clotting enzyme activity which results 74 μM of released p-nitroaniline concentration for 1 ng/mL of lentinan is detected, was used as the above described "fraction in which β-glucan-dependent clotting enzyme activity was detected".

f) Reagent for reaction 1: β-glucan-specific LAL fraction solution (31.25 volume), aqueous solution of the peptide derivative of the present invention (25 volume), 625 mM Tris-HCl buffer (pH 8.0) containing 625 mM magnesium sulfate (10 volume) and β-glucan-free water (33.75 volume) were mixed and used as the reagent for reaction 1 (concentration of the substrate of the present invention was 160 μM).

(ii) Study on the Reactivity with the Clotting Enzyme

Quantity of the decomposition product by β-glucan-specific LAL fraction was measured using the above-described reagent solution.

Namely, the reagent for reaction 1 (80 μL) was mixed with 25 ng/mL standard β-glucan solution (20 μL), and the solution was reacted at 37° C. for predetermined time, and then the reaction was terminated by adding 5 mM aqueous amidinophenyl benzoate hydrochloride solution (10 μL).

The solution in which the reaction was terminated was subjected to liquid chromatography [injection volume: 20 μL, Column: Wakosil ODS 5C18 (150 mmΦ×4.6 mm; produced by Wako Pure Chemical Industries Ltd.), mobile phase A: 0.1% aqueous trifluoroaceticacid solution, mobile phase B: acetonitrile containing 0.1% trifluoroacetic acid, gradient condition: rate of mobile phase A was 0% in 0 minutes→80% in 20 minutes→80% in 25 minutes, flow rate: 1 mL/minute, fluorescence detection wavelength: 647 nm], to measure an amount of the released fluorescent compound.

In addition, as a Comparative Example, amount of the released fluorescent compound was measured by the same method as the above-described method, using aqueous solution of the substrate analogous to the known substrate instead of the aqueous solution of the substrate of the present invention.

Figure 3:
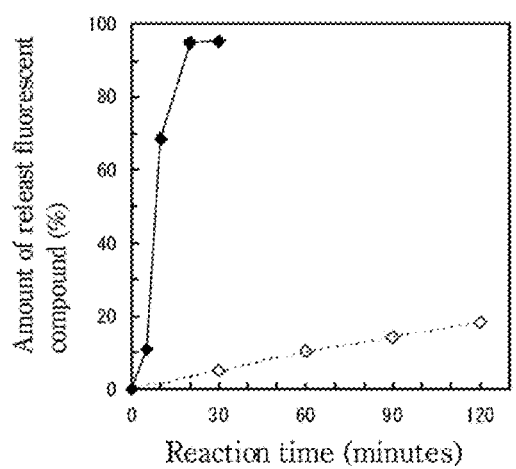
FIG. 3 shows the relationship between reaction time and amount of released fluorescent compound (area of released fluorescent compound versus total area), for the case where the substrate of the present invention is used and the case where the substrate obtained in Reference Example 1 is used. In addition, -♦- shows the result when the substrate of the present invention (Boc-Thr-Gly-Arg-Gly-NH(CH$_2$)$_4$NH-HiLyte647) was used, and -◇- shows the result when the known substrate (Boc-Thr-Gly-Arg-NH(CH$_2$)$_4$NH-HiLyte647) was used, respectively.

For the case when the aqueous solution of the substrate of the present invention is employed and the case when the aqueous solution of the substrate analogous to the known substrate is employed, the relationship between reaction time and amount of the released fluorescent compound (area of the released fluorescent compound versus total area) is shown in FIG. 3. In addition, -◆- shows the result when the substrate of the present invention (Boc-Thr-Gly-Arg-Gly-NH-(CH$_2$)$_4$-HiLyte647) is used, and -◇- shows the result when the substrate analogous to the known substrate (Boc-Thr-Gly-Arg-NH-(CH$_2$)$_4$-HiLyte647) obtained in Reference Example 1 is used, respectively.

As is clear from the results shown in FIG. 3, when the peptide derivative of the present invention is used as a substrate, said substrate was cleaved by the clotting enzyme in about 20 minutes, however, when the substrate obtained in Reference Example 1 is used, namely when the substrate in which the fluorescent group (or chromophore group) in the conventionally used tripeptide type substrate was substituted by the fluorescent dye-derived substituent of the present invention is used, its decomposition rate was 20% or lower even after 2 hours of reaction. From this result, it turned out that the substrate of the present invention was cleaved much faster than the conventional tripeptide type substrate by the effect of the amebocyte lysate of a horseshoe crab which had been reacted with β-glucan, that is, by the activated clotting enzyme.

Example 2

Quantitative Determination Method for (1→3)-β-D-glucan using the Peptide Derivative of the Present Invention as a Substrate

[Separation and Measurement by Microchip Electrophoresis]

(i) Preparation of Various Kinds of Reagent Solutions

Aqueous solution of the substrate of the present invention, β-glucan-free water, standard β-glucan solution and β-glucan specific LAL fraction solution were the same reagent solutions as in Experimental Example 1 (i).

a) Reagent for reaction 2: A mixed solution comprising β-glucan specific LAL fraction solution (50 volume), 32% trehalose solution (1.5625 volume), 20% polyethylene glycol 6000 (2.5 volume), aqueous solution of the peptide derivative of the present invention (0.0625 volume), 0.75 M Tris-HCl buffer (pH 8.0) containing 0.5 M magnesium chloride (20 volume) and β-glucan-free water (25.875 volume) was used as reagent for reaction 2 (concentration of the substrate of the present invention: 400 nM).

b) Reaction stop solution: 1.25 mM aqueous amidinophenyl benzoate hydrochloride solution comprising 2.5% Poly(N,N-dimethylacrylamide) (hereinafter, referred to as pDMA), 2.5% glycerol, 0.25% Tween20, 0.05% bovine serum albumin, and 5% heparin lithium was employed.

(ii) Reaction of the Standard β-glucan Solution with the Reagents

Predetermined concentration of the standard β-glucan solution (0, 1, 3, 10, 30, 100, 300 pg lentinan/mL) (50 μL) and the reagent for reaction 2 (50 μL) was mixed, and the solution was reacted at 30° C. for 5 minutes. Immediately after completion of the reaction, the reaction stop solution (25 μL) was added to terminate the reaction.

The solution after terminating the reaction was used as a sample and was subjected to the microchip electrophoresis as follows, and the enzymatic released product from the peptide derivative of the present invention generated by β-glucan specific LAL fraction and undigested peptide derivative of the present invention were separated, and amount of the enzymatic released product from the peptide derivative of the present invention was determined.

(iii) Electrophoresis
(iii-1) Capillary Tip

The capillary tip having a layout shown in FIG. 4 was prepared as follows according to the method described in Takehiko Kitamori, et al. "Technology and Application of Microscience Chip", p. 185-217, published 2004, (Maruzen Co., Ltd.)

That is, a photoresist film was formed on a Si film which has been formed on a quartz substrate. This photoresist was exposed to light using a mask which had a capillary design (layout) shown in FIG. 4, then washed out. After removing Si by sputtering in the area where photoresist had been removed by washing out, wet etching was carried out using hydrogen fluoride solution to produce grooves of capillary channel (fine canal) on the quartz substrate. After removing the photoresist and Si films remaining on the quartz substrate, said quartz substrate and a cover plate which had holes for introducing or discharging various reagents into various well were stuck together by high-frequency gluing method, to produce the capillary tip.

Figure 4:
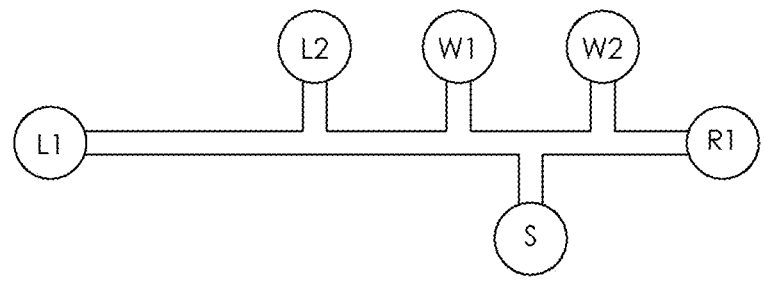
FIG. 4 shows a layout of capillary chip.

In addition, in FIG. 4, L1 and L2 show the wells for introducing leading buffer, R1 shows the well for introducing trailing buffer, S shows the well for introducing sample for electrophoresis, and W1 and W2 show the wells for drain, respectively. Further, in FIG. 4, the distance between L1 and R1 is 6.3 cm, and the distance between L1 and L2 is 2.8.

(iii-2) Sample for Electrophoresis
a) Trailing buffer: 125 mM HEPPSO containing 75 mM Tris base, 0.5% pDMA22, 3% Glycerol, 0.05% Tween20 and 0.01% BSA
b) Leading buffer: 75 mM Tris-HCl (pH 8) containing 50 mM NaCl, 0.5% pDMA22, 3% Glycerol, 0.05% Tween20, 0.01% BSA and 1% Heparin Li (iii-3) Introduction of Sample for Electrophoresis and Test Solution The solution (10 µL) after terminating the reaction obtained in the above-described (ii) was dispensed into S well (well for introducing sample for electrophoresis) in FIG. 4; the trailing buffer (10 µL) was dispensed into R1 well (well for introducing test solution); and the leading buffer (10 µL each) was dispensed into L1 well and L2 well, respectively, and then, −5 psi of pressure was applied between W1 (well for drain) and W2 (well for drain) for 100 seconds, to introduce the sample for electrophoresis and the leading buffer into the channel.

Figure 5:
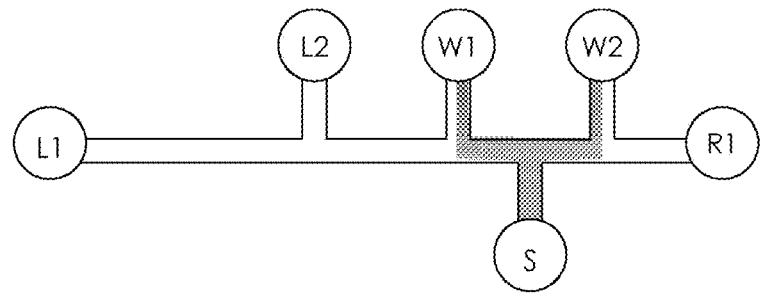
FIG. 5 shows a layout of a sample for electrophoresis and a test solution in the capillary.

Layout of a sample for electrophoresis and a test solution in the capillary is shown in FIG. 5 schematically. Here, the shaded part in FIG. 5 shows the area arranged for the sample for electrophoresis.

(iii-4) Concentration, Separation and Detection

A voltage of 2000 V was applied between R1 well and L1 well in FIG. 4, and the sample for electrophoresis was concentrated in the direction of R1→L1 at 10° C. When the sample for electrophoresis passed through the crossing part of the main channel and L2 channel, a voltage of 1000 V was applied between L2 well and L1 well to migrate in the direction of L2→L1, and thereby the peptide derivative of the present invention in said sample and the enzymatic released fluorescent compound from the peptide derivative of the present invention were separated, and the released fluorescent compound was detected.

In addition, detection was carried out at the position 2 cm away from the crossing point of L2 channel toward L1 in the capillary, by measuring fluorescence intensity with time by 650 nm laser excitation using a fluorescence microscope (BX-50; produced by KS Olympus Co., Ltd.).

[Measurement Results]

Figure 6:
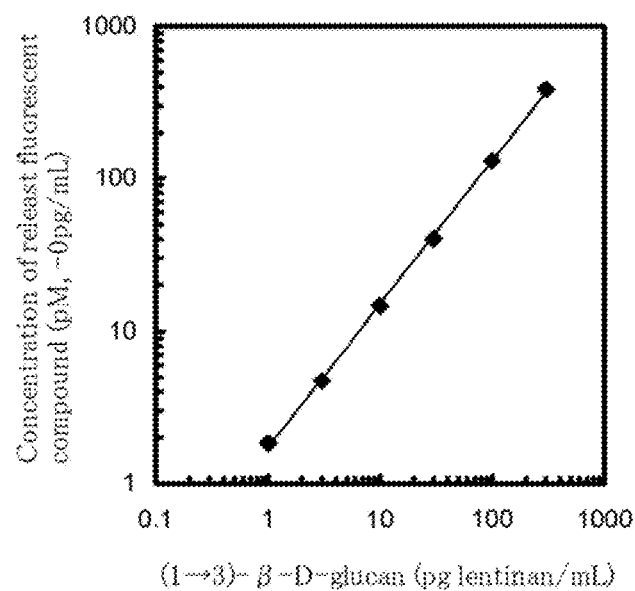
FIG. 6 is a graph showing the relationship between the concentration of released fluorescent compound from the peptide derivative of the present invention and the concentration of β-glucan when separation measurement was carried out by the microchip electrophoresis.

The relationship between the concentration of the enzymatic released fluorescent compound from the peptide derivative of the present invention and the concentration of β-glucan which was obtained by the above measurement is shown in FIG. 6. From these results, it turned out that there was a linear relationship between the concentration of the enzymatic released fluorescent compound and the β-glucan, and that if the β-glucan is measured by the method as described above using the peptide derivative of the present invention as a substrate, even if reaction time was 5 minutes, quantitative determination of β-glucan was possible. Furthermore, it turned out that β-glucan could be determined in minute scale of pg/mL, enabling high sensitivity measurement.

Example 3

Quantitative Determination Method for (1→3)-β-D-glucan using the Peptide Derivative of the Present Invention as a Substrate

[Separation and Measurement by Liquid Chromatography]
(i) Preparation of Various Kinds of Reagent Solutions Aqueous solution of the substrate of the present invention, (1→3)-β-D-glucan-free water, standard (1→3)-β-D-glucan solution and (1→3)-β-D-glucan specific LAL fraction and reaction stop solution were the same reagent solutions as described in Example 2 (i).

a) Reagent for reaction 3: A mixed solution comprising (1→3)-β-D-glucan specific LAL fraction solution (31.25 volume), aqueous solution of the peptide derivative of the present invention (25 volume), 1 M Tris-HCl buffer (pH 8.0) containing 1 M magnesium sulfate (6.25 volume) and β-glucan-free water (37.5 volume) was used as a reagent for reaction 3 (concentration of the substrate of the present invention: 160 µM).

(ii) Liquid Chromatography

Each of predetermined concentrations of the standard β-glucan solutions (0, 15, 50, 150, 500, 1500, 5000 pg lentinan/mL) (20 µL each) and the reagent for reaction 3 (80 µL) was mixed, and the solution was reacted at 37° C. for 30 minutes. Immediately after completion of the reaction, the reaction stop solution (25 µL) was added to terminate the reaction.

The solution after terminating the reaction was subjected to a liquid chromatography [injection volume: 20 µL, Column: Wakosil ODS 5C18 (150 mmφ×4.6 mm; produced by Wako Pure Chemical Industries Ltd.), mobile phase A: 0.1% aqueous trifluoroacetic acid solution, mobile phase B: acetonitrile containing 0.1% trifluoroacetic acid, gradient condition: rate of mobile phase A was 0% in 0 minutes→80% in 20 minutes→80% in 25 minutes, flow rate: 1 mL/minute, fluorescence detection wavelength: 647 nm], to determine the amount of the released fluorescent compound from the substrate.

Figure 7:
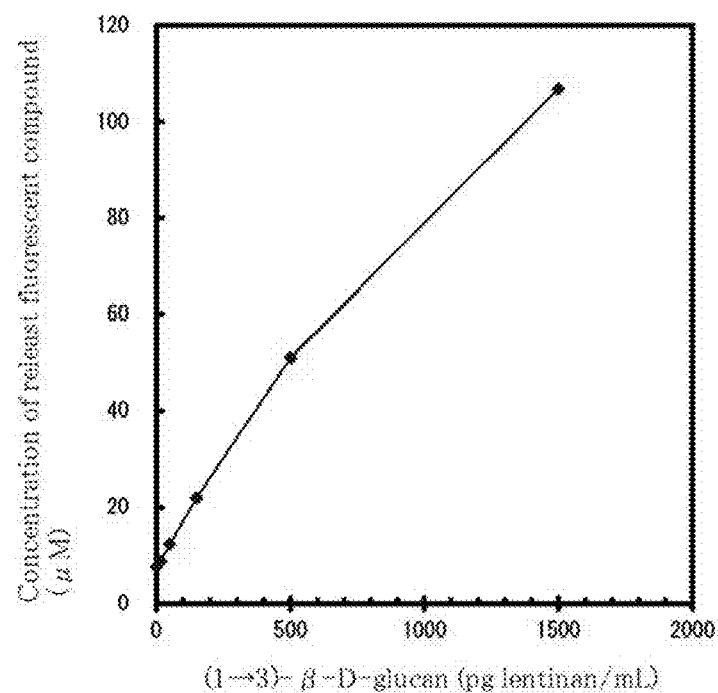
FIG. 7 is a graph showing the relationship between the concentration of enzymatic released fluorescent compound from the peptide derivative of the present invention and the concentration of β-glucan when separation measurement was carried out by HPLC.

The relationship between concentration of the enzymatic released fluorescent compound from the peptide derivative of the present invention and concentration of (1→3)-β-D-glucan which was obtained by the above measurement is shown in FIG. 7. From these results, it turned out that even if the peptide derivative of the present invention was used as a substrate and HPLC as described above was used, (1→3)-β-D-glucan could be measured in high sensitivity.

The invention claimed is:

1. A peptide derivative represented by formula (1):

X-$A_1$-Gly-Arg-Gly-E-D     (1)

wherein
X represents an N-terminal protecting group of amino acid,
$A_1$ represents a leucine residue, isoleucine residue, serine residue, or threonine residue,
Gly represents a glycine residue,
Arg represents an arginine residue,
D represents a fluorescent dye comprising a functional group, and
E represents a binding arm or a spacer which is derived from a compound represented by formula (3):

$R_1$-A-$R_2$     (3)

wherein $R_1$ represents a group having reactivity with a carboxyl group, A represents a straight-chain alkylene group having 1 to 6 carbon atoms, and $R_2$ represents a group having reactivity with the functional group present in the fluorescent dye represented by D.

2. The peptide derivative according to claim 1, wherein $A_1$ is a threonine residue.

3. The peptide derivative according to claim 1, wherein the N-terminal protecting group represented by X is selected from acetyl group, benzoyl group, benzyloxycarbonyl group, tosyl group, glutaryl group and t-butoxycarbonyl group.

4. The peptide derivative according to claim 1, wherein the dye in the fluorescent dye represented by D has an excitation wavelength of 500 nm to 800 nm.

5. The peptide derivative according to claim 1, wherein the fluorescent dye represented by D is cyanine dye.

6. The peptide derivative according to claim 1, wherein the peptide derivative represented by formula (1) is a compound represented by the formula:

Boc-Thr-Gly-Arg-Gly-NH—$(CH_2)_4$—NH-D wherein Boc represents t-butoxycarbonyl group and Thr represents a threonine residue.

7. A reagent for determining the presence or absence of, or for quantifying, β-glucan and/or endotoxin in a sample, comprising the peptide derivative according to claim 1.

8. A method for detecting or quantifying β-glucan and/or endotoxin comprising
reacting a sample containing β-glucan and/or endotoxin, an amebocyte lysate of a horseshoe crab, and the peptide derivative according to claim 1 under conditions suitable to cause the release of a compound represented by formula (2):

H-Gly-E-D     (2)

separating the compound represented by formula (2) from unreacted substance, and
quantifying the amount of the compound represented by formula (2),
thereby detecting or quantifying β-glucan and/or endotoxin based on the amount of the compound represented by formula (2).

9. The method according to claim 8, wherein the separation and quantification use capillary electrophoresis or liquid chromatography.

10. A reagent kit for detecting or quantifying β-glucan and/or endotoxin, comprising an amebocyte lysate of a horseshoe crab and the peptide derivative according to claim 1.

* * * * *